United States Patent
Berry

(10) Patent No.: US 11,678,994 B2
(45) Date of Patent: Jun. 20, 2023

(54) COMPLIANT SPINAL IMPLANT

(71) Applicant: Bret Michael Berry, Tallahassee, FL (US)

(72) Inventor: Bret Michael Berry, Tallahassee, FL (US)

(*) Notice: Subject to any disclaimer, the term of this patent is extended or adjusted under 35 U.S.C. 154(b) by 26 days.

(21) Appl. No.: 17/109,092

(22) Filed: Dec. 1, 2020

(65) Prior Publication Data

US 2022/0168114 A1 Jun. 2, 2022

(51) Int. Cl.
*A61F 2/44* (2006.01)
*A61F 2/30* (2006.01)

(52) U.S. Cl.
CPC .......... *A61F 2/442* (2013.01); *A61F 2/30771* (2013.01); *A61F 2002/3093* (2013.01); *A61F 2002/30125* (2013.01); *A61F 2002/30841* (2013.01); *A61F 2002/443* (2013.01)

(58) Field of Classification Search
CPC .......... A61F 2/442; A61F 2/44; A61F 2/4455; A61F 2002/30125; A61F 2002/30841; A61F 2002/3093; A61F 2002/443
USPC ............................................. 623/17.11–17.16
See application file for complete search history.

(56) References Cited

U.S. PATENT DOCUMENTS

| | | | | |
|---|---|---|---|---|
| 4,309,777 A * | 1/1982 | Patil | ........................ | A61F 2/442 606/907 |
| 7,309,357 B2 * | 12/2007 | Kim | ........................ | A61F 2/442 623/17.13 |
| 9,039,766 B1 * | 5/2015 | Fonte | .................... | A61F 2/3094 623/17.13 |
| 2004/0002761 A1 * | 1/2004 | Rogers | .................. | A61F 2/4425 623/17.13 |
| 2005/0113924 A1 * | 5/2005 | Buttermann | ....... | A61B 17/1671 623/17.13 |
| 2006/0149381 A1 * | 7/2006 | Kim | ........................ | A61F 2/442 623/17.13 |
| 2006/0200240 A1 * | 9/2006 | Rothman | ................ | A61F 2/442 623/17.13 |
| 2008/0077246 A1 * | 3/2008 | Fehling | .................... | A61F 2/442 623/17.13 |
| 2009/0076614 A1 * | 3/2009 | Arramon | ............... | A61F 2/4425 623/17.11 |
| 2009/0192617 A1 * | 7/2009 | Arramon | ............... | A61F 2/4425 623/17.13 |
| 2009/0292363 A1 * | 11/2009 | Goldfarb | ................ | A61F 2/442 623/17.13 |
| 2010/0114318 A1 * | 5/2010 | Gittings | ................ | A61F 2/4425 606/246 |
| 2020/0289285 A1 * | 9/2020 | Siemionow | ........ | A61B 17/7064 |

* cited by examiner

*Primary Examiner* — Jessica Weiss
(74) *Attorney, Agent, or Firm* — McCarter & English, LLP; James Smedley; Alex Korona

(57) ABSTRACT

The present invention relates generally to prosthetic spinal implants. Specifically, the present invention relates to a compliant implant for spinal intervertebral disc replacement.

13 Claims, 4 Drawing Sheets

COMPLIANT SPINAL IMPLANT

FIELD OF THE INVENTION

The present invention relates generally to prosthetic spinal implants. Specifically, the present invention relates to a compliant implant for spinal intervertebral disc replacement.

BACKGROUND OF THE INVENTION

Intervertebral discs function to permit limited motion and flexibility of the spine, while having the ability to maintain segmental stability, absorb and distribute external loads. The structure and function of intervertebral discs may be altered by physiological aging, trauma, repetitive stress, segmental instability of the spine, and other inflammatory or biochemical factors. Approaches aimed at restoring the function of degenerated or dysfunctional intervertebral discs include procedures for replacing degenerated or dysfunctional discs with artificial or prosthetic discs.

Consequently, various prosthetic intervertebral discs have been developed for positioning between adjacent spinal segments. However, many of the current designs for prosthetic intervertebral discs are large and inflexible and provide minimal articulation. Therefore, there is a need in the art for a compliant intervertebral implant that can bend and flex to permit a spine to transmit motion through the implant, and is able to compress similar to a healthy intervertebral disc, when and where a load is applied. The present invention is provided to solve the problems discussed above and other problems, and to provide advantages and features not provided by currently available prosthetic intervertebral discs. These and other features and advantages of the present invention will be explained and will become obvious to one skilled in the art through the summary of the invention that follows.

SUMMARY OF THE INVENTION

The present invention relates generally to a prosthetic spinal implant for replacing a spinal disc between two vertebrae of a spine. In particular, the present invention encompasses a prosthetic spinal disc with compliant components. These compliant components may be configured to allow the implant to flex and bend, and may comprise a thickness sufficient to provide stability and prevent breakage of the implant structure.

BRIEF DESCRIPTION OF THE DRAWINGS

Accompanying this written specification is a collection of drawings of exemplary embodiments of the present invention. One of ordinary skill in the art would appreciate that these are merely exemplary embodiments, and additional and alternative embodiments may exist and still be within the spirit of the invention as described herein.

DETAILED DESCRIPTION OF THE DRAWINGS

Figure 1:
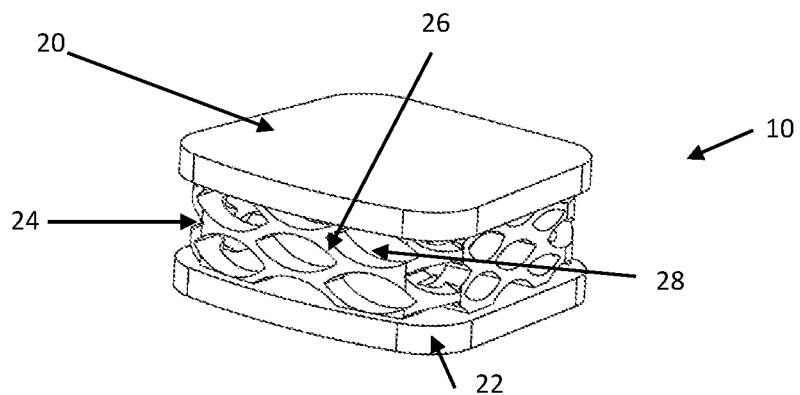
FIG. 1 is a perspective view of a compliant spinal implant in accordance with a first embodiment of the present invention.

In the Summary above and in this Detailed Description, and the claims below, and in the accompanying drawings, reference is made to particular features of various embodiments of the invention. It is to be understood that the disclosure of embodiments of the invention in this specification includes all possible combinations of such particular features. For example, where a particular feature is disclosed in the context of a particular aspect or embodiment of the invention, or a particular claim, that feature can also be used—to the extent possible—in combination with and/or in the context of other particular aspects and embodiments of the invention, and in the invention generally.

While multiple embodiments are disclosed, still other embodiments of the present invention will become apparent to those skilled in the art from this detailed description. The invention is capable of myriad modifications in various obvious aspects, all without departing from the spirit and scope of the present invention. Accordingly, the drawings and descriptions are to be regarded as illustrative in nature and not restrictive.

In accordance with embodiments of the present invention, a compliant spinal implant may be configured to be implanted into a spine, to imitate the functions of a healthy spinal disc, for example, to provide and permit the same or similar mobility and load carrying ability of a healthy spinal disc. The compliant spinal implant may comprise one or more compliant components configured to bend and flex to permit a spine within which the implant is inserted to transmit motion through the implant. The compliant components may be configured to have a sufficient thickness, to provide sufficient stability and prevent breakage of the implant structure. The compliant components may be made from any suitable material, including but not limited to titanium, cobalt chrome, nitinol, and other materials that would be obvious to one of ordinary skill in the art.

In accordance with embodiments of the present invention, a prosthetic implant may comprise a pair of endplate components, each having an exterior face opposing an interior face. The exterior face of each endplate component may be adapted to engage with bone while the interior face may be formed with one or more compliant components configured to connect the pair of endplate components. In some embodiments, the compliant components may comprise one or more strut elements. In some embodiments, the compliant components may comprise one or more voids. In some embodiments, the voids may be substantially oval or almond-shaped In accordance with embodiments of the present invention, a prosthetic implant may comprise one or more compliant components forming a mesh-type web having a structure defined by an alternating or repeating pattern of substantially oval or almond-shaped voids. In some embodiments, the compliant components form a mesh-type framework comprising a plurality of strut elements sequentially distanced by a plurality of voids or openings.

In accordance with embodiments of the present invention, a prosthetic implant may comprise a pair of endplate components, each having an exterior face opposing an interior face, the exterior face adapted to engage with bone and the interior face having a compliant framework extending therefrom to connect the pair of endplate components, the framework comprising a plurality of interconnected strut elements and a plurality of voids. In some embodiments, the strut elements may be separated from one another by the voids. In some embodiments, the strut elements may be substantially oval or almond-shaped. In some embodiments, the framework may be formed of a compliant material. In some embodiments, the framework may be a mesh-type structure. In some embodiments, the framework may be disposed around the periphery of the interior face and may enables the implant to bend or flex in a manner that replicates or is substantially similar to axial rotation.

In accordance with embodiments of the present invention, a prosthetic implant may comprise a pair of endplate components, each having an exterior face opposing an interior face, the exterior face adapted to engage with bone and the interior face formed with one or more compliant components comprising one or more strut elements formed as bands with one or more curves and bends, the compliant components configured to connect the pair of endplate components. In some embodiments, each strut element may have a first end with one or more first endplate connection points connected to a first endplate component and a second end with one or more second endplate connection points connected to a second endplate component. In some embodiments, each strut element may be flexible and may be configured to curve and bend between each of the strut element first and second ends.

Turning now to the Figures, FIG. 1 depicts a perspective view of a compliant spinal implant in accordance with a first embodiment of the present invention. As shown in FIG. 1, a compliant spinal implant 10 may comprise a first endplate component 20 and a second endplate component 22. In the illustrated example, one or more compliant components 24 connect the first endplate component 20 to the second endplate component 22. As shown in the depicted example, the compliant components 24 may comprise one or more strut elements 26 and one or more voids 28. In some examples, the compliant components 24 may be arranged in a web, network or matrix configuration. In some embodiments, the strut elements 26 may be thin enough to permit the flexing and bending of the compliant components 24, but may have a sufficient thickness to prevent breakage of the compliant components 24 or the structure of the implant 10. The first and second endplate components 20 and 22 are contemplated to have the orientation of any geometric shape, including: squares, rectangles, circles, ovals, pentagons, hexagons and triangles. One of ordinary skill in the art would appreciate that there are numerous suitable and advantageous arrangements for the geometric orientation of the first and second endplate components depending on the specific intended use application of the particular compliant spinal implant and embodiments of the present invention are contemplated for use with any such compliant spinal implant arrangements.

Figure 2:
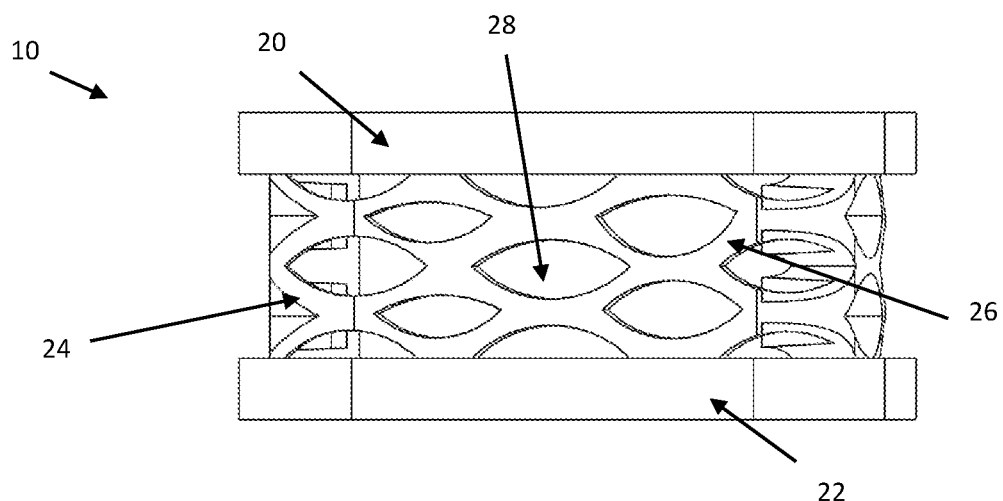
FIG. 2 is a front view of a compliant spinal implant in accordance with a first embodiment of the present invention.

FIG. 2 depicts a front view of a compliant spinal implant in accordance with a first embodiment of the present invention. As shown in FIG. 2, the compliant spinal implant 10 may comprise a first endplate component 20 connected to a second endplate component 22 by one or more compliant components 24. The compliant components 24 may comprise one or more strut elements 26 and one or more voids 28. As shown in FIGS. 1 and 2, in some embodiments, the compliant components 24 may be disposed around the periphery of the inner surfaces of the first and second endplate components 20 and 22, respectively.

Figure 3:
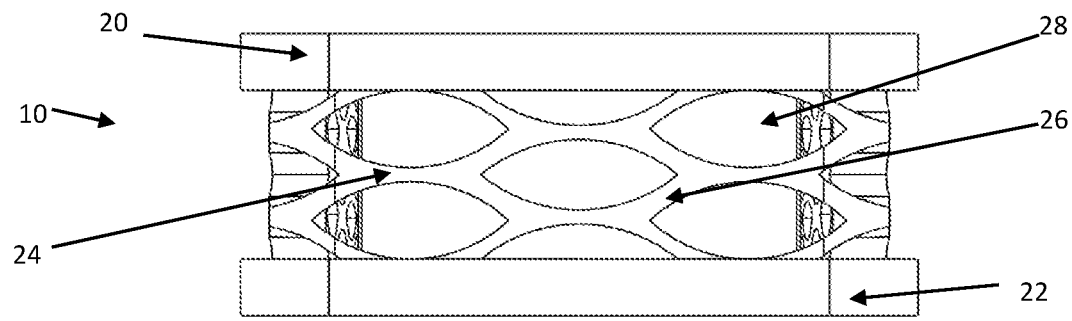
FIG. 3 is a side view of a compliant spinal implant in accordance with a first embodiment of the present invention.

FIG. 3 depicts a side view of a compliant spinal implant in accordance with a first embodiment of the present invention. As shown in FIG. 3, the compliant components 24 may comprise one or more strut elements 26 separated by one or more substantially oval or almond-shaped voids 28. In any embodiment, the voids 28 are contemplated to have the orientation of any geometric shape, including: squares, rectangles, circles, pentagons, hexagons or triangles. One of ordinary skill in the art would appreciate that there are numerous suitable and advantageous arrangements for the geometric orientation of the voids depending on the specific intended use application of the particular compliant spinal implant and embodiments of the present invention are contemplated for use with any such compliant spinal implant arrangements.

In accordance with embodiments of the present invention, the compliant components 24 may comprise a mesh-type framework comprising a plurality of strut elements 26 sequentially distanced by a plurality of voids or openings 28. In any embodiment, the framework may be configured as a web or net-like framework.

In accordance with embodiments of the present invention, the compliant components 24 may be configured to compress in a region where a load is applied, permitting the implant 10 to bend in the sagittal or lateral planes, or any combination of the two. Moreover, the placement of the compliant components 24 between the first and second endplate components 20 and 22, for example, around the periphery of the internal surfaces of the first and second endplate components 20 and 22, may enable the implant 10 to bend or flex in a manner that replicates or is substantially similar to axial rotation. In some embodiments, the compliant components 24 may be configured to permit the implant 10 to stretch or expand.

Figure 4:
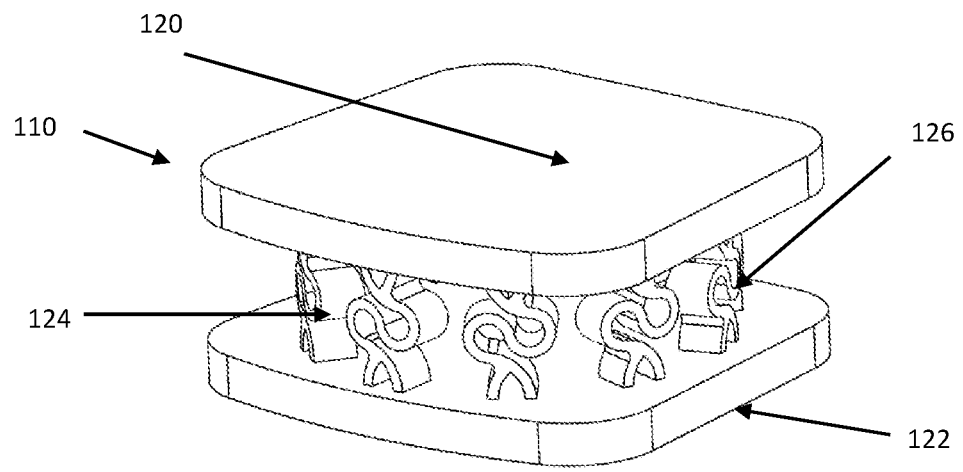
FIG. 4 is a perspective view of a compliant spinal implant in accordance with a second embodiment of the present invention.

FIG. 4 depicts a perspective view of a compliant spinal implant in accordance with a second embodiment of the present invention. As shown in FIG. 4, a compliant spinal implant 110 may comprise a first endplate component 120 and a second endplate component 122. In the illustrated example, one or more compliant components 124 connect the first endplate component 120 to the second endplate component 122. As shown in the depicted example, the compliant components 124 may comprise one or more strut elements 126 or one or more series of strut elements 126. As shown in the depicted example, the strut elements 126 may comprise bends, arcs, curves, loops, twists or coils. In the preferred embodiment, the unique curved and bent shape of the strut elements 126 enable bending of the implant 110 in selected or preferred directions. As demonstrated in the illustrated example, the strut elements 126 may be thin enough to permit the flexing and bending of the compliant components 124, but may have a sufficient thickness to prevent breakage of the compliant components 124 or the structure of the implant 110. The first and second endplate components 120 and 122 are contemplated to have the orientation of any geometric shape, including: squares, rectangles, circles, ovals, pentagons, hexagons or triangles. One of ordinary skill in the art would appreciate that there are numerous suitable and advantageous arrangements for the geometric orientation of the first and second endplate components depending on the specific intended use application of the particular compliant spinal implant and embodiments of the present invention are contemplated for use with any such compliant spinal implant arrangements.

Figure 5:
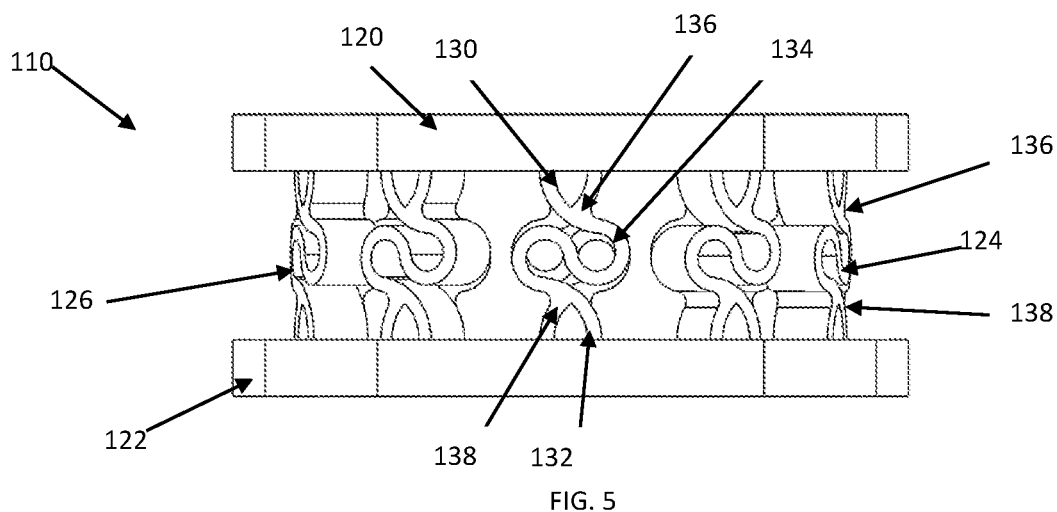
FIG. 5 is a front view of a compliant spinal implant in accordance with a second embodiment of the present invention.
Figure 6:
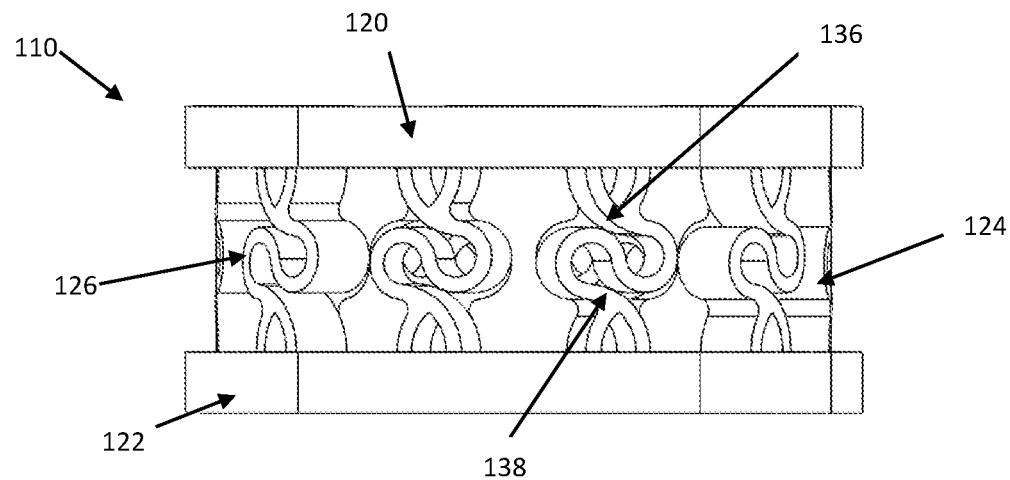
FIG. 6 is a side view of a compliant spinal implant in accordance with a second embodiment of the present invention.

FIG. 5 and FIG. 6 respectively depict front and side views of a compliant spinal implant in accordance with a second embodiment of the present invention. As shown in FIG. 5, the compliant spinal implant 110 may comprise a first endplate component 120 connected to a second endplate component 122 by one or more compliant components 124. As shown in FIGS. 4 and 5, in some embodiments, the compliant components 124, for example, the strut elements 126, may be disposed around the periphery of the inner surfaces of the first and second endplate components 120 and 122, respectively.

Figure 7:
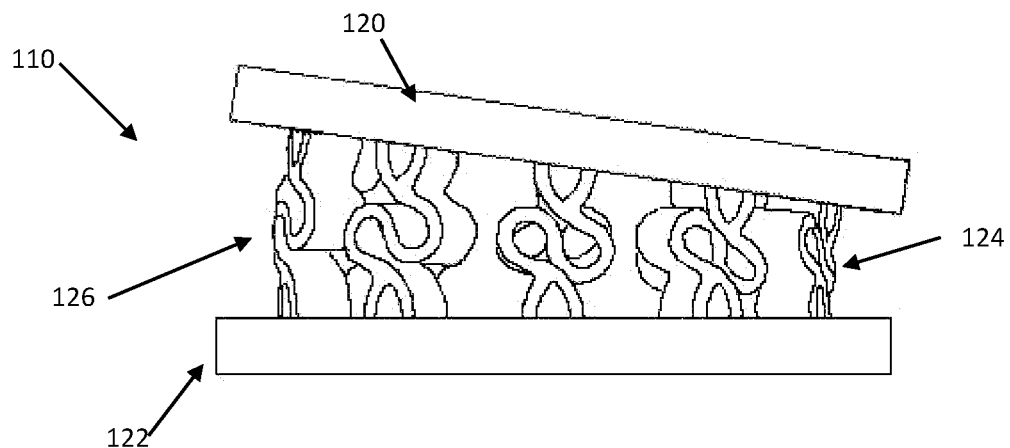
FIG. 7 is a front view of a compliant spinal implant under an external pressure to demonstrate the flexibility and compliance of the implant in accordance with a second embodiment of the present invention.
Figure 8:
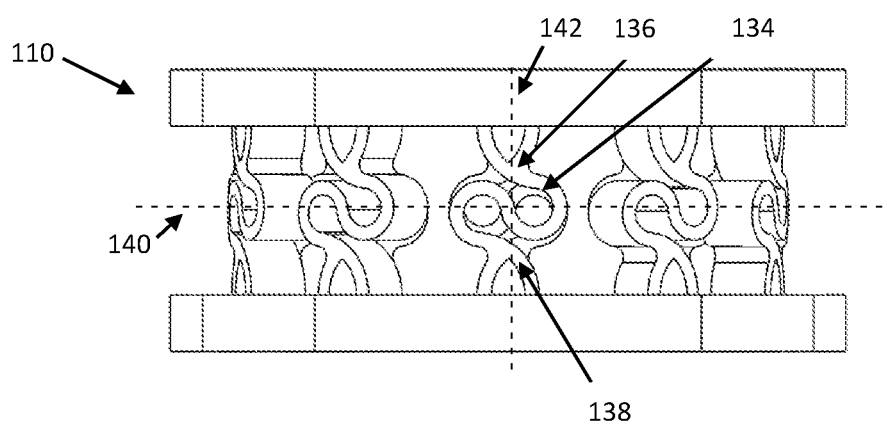
FIG. 8 is a front view of a compliant spinal implant demonstrating longitudinal axes of u-shaped and serpentine segments of the compliant spinal implant in accordance with a second embodiment of the present invention.

FIG. 7 depicts a front view of a compliant spinal implant under an external pressure to demonstrate the flexibility and compliance of the implant in accordance with a second embodiment of the present invention. As shown in FIG. 7, the compliant components 124 may be configured to compress in a region where a load is applied, permitting the implant 110 to bend in the sagittal or lateral planes, or any combination of the two. FIG. 7 further demonstrates how the strut elements 126 can bend under specific loads, for example, as shown in FIG. 7, lateral bending. As shown in the illustrated example, while the strut elements 126 under the load demonstrated by downward arrows react to the force with compression, the strut elements 126 on the opposite side of the implant 110 may stretch or expand. In some scenarios, this configuration permits the compliant components 124 to substantially replicate the motion of spinal discs, for example, human intervertebral discs.

As shown in the depicted examples, in some embodiments, a prosthetic implant 110 may comprise a first endplate 120 and a second endplate 122, each having an exterior face and an opposing interior face, wherein each of the exterior faces is adapted to engage with bone; and a plurality of strut elements 126 that connect the interior face of the first endplate 120 to the interior face of the second endplate 122, wherein each of the strut elements 126 has a first U-shaped segment 130 connected to the interior face of the first endplate 120, a second U-shaped segment 132 connected to the interior face of the second endplate 122, and a serpentine segment 134 connecting between the first and second U-shaped segments 130, 132 such that each strut element 126 extends from both the interior face of the first endplate 120 and the interior face of the second endplate 122. In some examples, each of the U-shaped segments 130, 132 may be connected to the interior face of the respective first or second endplate 120, 122 at two points. In some embodiments, the serpentine segment 134 of each of the strut elements 126 may connect between an apex 136 of the first U-shaped segment 130 and an apex 138 of the second U-shaped segment 132, and a longitudinal axis 140 of the serpentine segment 134 may be perpendicular to a longitudinal axis 142 of each of the U-shaped segments 130, 132 to which the serpentine segment 134 is attached when the prosthetic implant 110 is in an uncompressed state.

In some embodiments, the first and second U-shaped segments 130, 132 may be longitudinally bisected by a common axis 142 running through an apex of each of the first and second U-shaped segments when the prosthetic implant is in an uncompressed state.

In some embodiments, an apex 136 of the first U-shaped segment 130 may be at an opposite end of the first U-shaped segment 130 from where the first U-shaped segment 130 attaches to the interior face of the first endplate 120. Similarly, an apex 138 of the second U-shaped segment 132 may be at an opposite end of the second U-shaped segment 132 from where the second U-shaped segment 132 attaches to the interior face of the second endplate 122.

In any embodiment, any portion of the exterior surface of the endplate components may comprise a means for attaching or fastening the implant to bone or vertebrae. In some examples, the means for attaching or fastening the implant to bone or vertebrae may be or comprise porous ingrowth surface, plasma spray surface, roughened surface, or sharpened protrusions such as teeth, keels, spikes, or any combination of the foregoing. One of ordinary skill in the art would appreciate that there are numerous suitable and advantageous arrangements for the geometric orientation of the first and second bases depending on the specific intended use application of the particular interlocking prosthetic spinal disc and embodiments of the present invention are contemplated for use with any such prosthetic spinal disc arrangements.

It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments.

In the present disclosure, various features may be described as being optional, for example, through the use of the verb "may;", or, through the use of any of the phrases: "in some embodiments," "in some implementations," "in some designs," "in various embodiments," "in various implementations,", "in various designs," "in an illustrative example," or "for example;" or, through the use of parentheses. For the sake of brevity and legibility, the present disclosure does not explicitly recite each and every permutation that may be obtained by choosing from the set of optional features. However, the present disclosure is to be interpreted as explicitly disclosing all such permutations. For example, a system described as having three optional features may be embodied in seven different ways, namely with just one of the three possible features, with any two of the three possible features or with all three of the three possible features.

In various embodiments elements described herein as coupled or connected may have an effectual relationship realizable by a direct connection or indirectly with one or more other intervening elements.

In the present disclosure, the term "any" may be understood as designating any number of the respective elements, i.e. as designating one, at least one, at least two, each or all of the respective elements. Similarly, the term "any" may be understood as designating any collection(s) of the respective elements, i.e. as designating one or more collections of the respective elements, a collection comprising one, at least one, at least two, each or all of the respective elements. The respective collections need not comprise the same number of elements.

While various embodiments of the present invention have been disclosed and described in detail herein, it will be apparent to those skilled in the art that various changes may be made to the configuration, operation and form of the invention without departing from the spirit and scope thereof. In particular, it is noted that the respective features of embodiments of the invention, even those disclosed solely in combination with other features of embodiments of the invention, may be combined in any configuration excepting those readily apparent to the person skilled in the art as nonsensical. Likewise, use of the singular and plural is solely for the sake of illustration and is not to be interpreted as limiting.

In the present disclosure, all embodiments where "comprising" is used may have as alternatives "consisting essentially of," or "consisting of." In the present disclosure, any method or apparatus embodiment may be devoid of one or more process steps or components. In the present disclosure, embodiments employing negative limitations are expressly disclosed and considered a part of this disclosure.

Certain terminology and derivations thereof may be used in the present disclosure for convenience in reference only and will not be limiting. For example, words such as "upward," "downward," "left," and "right" would refer to directions in the drawings to which reference is made unless otherwise stated. Similarly, words such as "inward" and "outward" would refer to directions toward and away from, respectively, the geometric center of a device or area and designated parts thereof. References in the singular tense include the plural, and vice versa, unless otherwise noted.

The term "comprises" and grammatical equivalents thereof are used herein to mean that other components, ingredients, steps, among others, are optionally present. For example, an embodiment "comprising" (or "which comprises") components A, B and C can consist of (i.e., contain only) components A, B and C, or can contain not only components A, B, and C but also contain one or more other components.

Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example, "at least 1" means 1 or more than 1. The term "at most" followed by a number (which may be a range having 1 or 0 as its lower limit, or a range having no lower limit, depending upon the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose limit is the second number. For example, 25 to 100 mm means a range whose lower limit is 25 mm and upper limit is 100 mm.

Many suitable methods and corresponding materials to make each of the individual parts of embodiment apparatus are known in the art. According to an embodiment of the present invention, one or more of the parts may be formed by machining, 3D printing (also known as "additive" manufacturing), CNC machined parts (also known as "subtractive" manufacturing), and injection molding, as will be apparent to a person of ordinary skill in the art. Metals, wood, thermoplastic and thermosetting polymers, resins and elastomers as may be described herein-above may be used. Many suitable materials are known and available and can be selected and mixed depending on desired strength and flexibility, preferred manufacturing method and particular use, as will be apparent to a person of ordinary skill in the art.

Any element in a claim herein that does not explicitly state "means for" performing a specified function, or "step for" performing a specific function, is not to be interpreted as a "means" or "step" clause as specified in 35 U.S.C. § 112 (f). Specifically, any use of "step of" in the claims herein is not intended to invoke the provisions of 35 U.S.C. § 112 (f).

A number of implementations have been described. Nevertheless, it will be understood that various modifications may be made. For example, advantageous results may be achieved if the steps of the disclosed techniques were performed in a different sequence, or if components of the disclosed systems were combined in a different manner, or if the components were supplemented with other components. Accordingly, other implementations are contemplated within the scope of the following claims.

What is claimed is:

1. A prosthetic implant, comprising:
a first endplate and a second endplate, each having an exterior face and an opposing interior face, wherein each of the exterior faces is adapted to engage with bone; and
a plurality of strut elements that connect the interior face of the first endplate to the interior face of the second endplate, wherein each of the strut elements has a first U-shaped segment connected to the interior face of the first endplate, a second U-shaped segment connected to the interior face of the second endplate, and a serpentine segment connecting between the first and second U-shaped segments such that each strut element extends from both the interior face of the first endplate and the interior face of the second endplate;
wherein each of the U-shaped segments is connected to the interior face of the respective first or second endplate at two points;
wherein the serpentine segment of each of the strut elements connects between an apex of the first U-shaped segment and an apex of the second U-shaped segment, and a longitudinal axis of each serpentine segment is perpendicular to a longitudinal axis of each of the U-shaped segments to which the serpentine segment is attached when the prosthetic implant is in an uncompressed state.

2. The prosthetic implant of claim 1, wherein the first and second U-shaped segments are longitudinally bisected by a common axis running through an apex of each of the first and second U-shaped segments when the prosthetic implant is in an uncompressed state.

3. The prosthetic implant of claim 1, wherein the plurality of strut elements are disposed around a periphery of the interior face of the first endplate and a periphery of the interior face of the second endplate.

4. The prosthetic implant of claim 1, wherein each of the strut elements is formed entirely independent from each of the other strut elements.

5. The prosthetic implant of claim 1, wherein the exterior surface of the first endplate and the exterior surface of the second endplate are each formed with one or more sharpened protrusions.

6. A prosthetic implant, comprising:
a first endplate and a second endplate, each having an exterior face and an opposing interior face, wherein each of the exterior faces is adapted to engage with bone; and a plurality of strut elements that connect the interior face of the first endplate to the interior face of the second endplate, wherein each of the strut elements is independently formed from each of the other strut elements and each of the strut elements has a first U-shaped segment connected to the interior face of the first endplate, a second U-shaped segment connected to the interior face of the second endplate, and a serpentine segment connecting between the first and second U-shaped segments such that each strut element extends from both the interior face of the first endplate and the interior face of the second endplate;

wherein the serpentine segment of each of the strut elements connects between an apex of the first U-shaped segment and an apex of the second U-shaped segment, and a longitudinal axis of each serpentine segment is perpendicular to a longitudinal axis of each of the U-shaped segments to which the serpentine segment is attached when the prosthetic implant is in an uncompressed state.

7. The prosthetic implant of claim 6, wherein each of the U-shaped segments is connected to the interior face of the respective first or second endplate at a first connection point and a second connection point.

8. The prosthetic implant of claim 7, wherein an apex of each of the U-shaped segments is at an opposite end of the U-shaped segment from where the U-shaped segment attaches to the interior face of the respective endplate.

9. The prosthetic implant of claim 6, wherein the plurality of strut elements are disposed around a periphery of the interior face of the first endplate and a periphery of the interior face of the second endplate.

10. The prosthetic implant of claim 9, wherein the exterior surface of the first endplate and the exterior surface of the second endplate each include one or more sharpened protrusions.

11. A prosthetic implant, comprising:
a first endplate and a second endplate, each having an exterior face and an opposing interior face, wherein each of the exterior faces is adapted to engage with bone; and
a plurality of strut elements that each extend from and connect between the interior face of the first endplate and the interior face of the second endplate, wherein each of the strut elements is independently formed from each of the other strut elements and each of the strut elements has a first U-shaped segment connected to a first and second connection point on the interior face of the first endplate, a second U-shaped segment connected to a first and second connection point on the interior face of the second endplate, and a serpentine segment connecting between an apex of the first U-shaped segment and an apex of the second U-shaped segment;

wherein a longitudinal axis of each serpentine segment is perpendicular to a longitudinal axis of each of the U-shaped segments to which the serpentine segment is attached when the prosthetic implant is in an uncompressed state.

12. The prosthetic implant of claim 11, wherein the plurality of strut elements are disposed around a periphery of the interior face of the first endplate and only around a periphery of the interior face of the second endplate.

13. The prosthetic implant of claim 11, wherein the plurality of strut elements enable the implant to bend or flex in a manner similar to a healthy spinal disc.

* * * * *